United States Patent
Gilmer et al.

(10) Patent No.: US 9,180,129 B2
(45) Date of Patent: Nov. 10, 2015

(54) COMBINATION OF LAPATINIB AND TRAMETINIB

(75) Inventors: Tona M. Gilmer, Research Triangle Park, NC (US); Rakesh Kumar, Collegeville, PA (US)

(73) Assignee: NOVARTIS AG, Basel (CH)

(*) Notice: Subject to any disclaimer, the term of this patent is extended or adjusted under 35 U.S.C. 154(b) by 0 days.

(21) Appl. No.: 13/699,077

(22) PCT Filed: May 19, 2011

(86) PCT No.: PCT/US2011/037146
§ 371 (c)(1),
(2), (4) Date: Nov. 20, 2012

(87) PCT Pub. No.: WO2011/146712
PCT Pub. Date: Nov. 24, 2011

(65) Prior Publication Data
US 2013/0109705 A1   May 2, 2013

Related U.S. Application Data

(60) Provisional application No. 61/347,081, filed on May 21, 2010, provisional application No. 61/374,343, filed on Aug. 17, 2010.

(51) Int. Cl.
| A61K 31/519 | (2006.01) |
| A61K 31/517 | (2006.01) |
| A01N 43/90 | (2006.01) |
| A01N 43/54 | (2006.01) |
| A61K 9/20 | (2006.01) |
| A61K 9/48 | (2006.01) |

(52) U.S. Cl.
CPC .............. *A61K 31/519* (2013.01); *A61K 9/2018* (2013.01); *A61K 9/2054* (2013.01); *A61K 9/4858* (2013.01); *A61K 31/517* (2013.01)

(58) Field of Classification Search
CPC ............ A61K 2300/00; A61K 31/517; A61K 31/4155; A61K 31/4375; A61K 31/519; A61K 9/2018; A61K 9/2054; A61K 9/4858; A61K 9/2059
USPC .............................. 514/264.1, 264.24, 266.24
See application file for complete search history.

(56) References Cited

U.S. PATENT DOCUMENTS

| 7,157,466 B2 * | 1/2007 | McClure et al. .......... 514/264.11 |
| 7,378,423 B2 * | 5/2008 | Kawasaki et al. .......... 514/264.1 |
| 2006/0014768 A1 | 1/2006 | Kawasaki et al. |
| 2010/0069411 A1 | 3/2010 | Butler et al. |

FOREIGN PATENT DOCUMENTS

| WO | WO 99/35146 | 7/1999 |
| WO | WO 02/02552 | 1/2002 |
| WO | WO 2005/121142 | 12/2005 |
| WO | WO2006/113649 | 10/2006 |

OTHER PUBLICATIONS

Walters, et al., *Neoplasia*, 15(2):143-155 (2013).
Zoppoli, et al., *Current Cancer Drug Targets*, 10(2):168-175 (2010).
Chan, *Current Opinion Immunology*, 8(3):394-401 (1996).
Chou, *Adv Enzyme Regul*, 22:27-55 (1984).
Cooper, *Semin. Cell. Biology*, 5(6):377-387 (1994).
Courtneidge, *Development Supp.*, 57-64 (1993).
Crews, et al., *Cell*, 74:215-217 (1993).
Hayashi, *Clinical Cancer Research*, 14(23):7843-7849 (2008).
Hemmings, *Science*, 277:534 (1997).
Hoshino, et al., *Journal of Biological Chemistry*, 276(4):2686-2692 (2001).
Kaya, *Eur. Journal of Gynaecology and Oncology*, 294):350-356 (2008).
Paulson, *Semin. Immunology*, 7(4:267-277 (1995).
Tanner, *Journal of Clinical Oncology*, 24(26):4317-4323 (2006).
Ullrich, et al., *Cell*, 61:203-212 (1990).
Wilks, *Progress in Growth Factor Research*, 2:97-111 (1990).
Woodburn, *Pharmacological Therapy*, 82:2-3, 241-250 (1999).
Greshock, Joel et al: "Molecular Target Class is Predictive of In vitro Response profile", Cancer Research, 2010, 70(9), pp. 3677-3686.

* cited by examiner

*Primary Examiner* — My-Chau T Tran
(74) *Attorney, Agent, or Firm* — Sandra Rueck

(57) ABSTRACT

The present invention relates to a method of treating cancer in a human and to pharmaceutical combinations useful in such treatment. In particular, the method relates to a cancer treatment method that includes administering N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate and/or salt thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, to a human in need thereof.

20 Claims, 2 Drawing Sheets

COMBINATION OF LAPATINIB AND TRAMETINIB

This application is a 371 of International Application No. PCT/US2011/037146, filed 19 May 2011, which claims priority to U.S. Provisional Application No. 61/347,081 filed on 21 May 2010, which claims priority to U.S. Provisional Application No. 61/374,343 filed 17 Aug. 2010

FIELD OF THE INVENTION

The present invention relates to a method of treating cancer in a mammal and to combinations useful in such treatment. In particular, the method relates to a novel combination comprising the dual EGF-R/erbB-2 inhibitor: N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate and/or salt thereof, and MEK inhibitor: N-{3-[3-cyclopropyl-5-(2-fluoro-4-iodophenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, pharmaceutical compositions comprising the same, and methods of using such combinations in the treatment of cancer.

BACKGROUND OF THE INVENTION

Generally, cancer results from the deregulation of the normal processes that control cell division, differentiation and apoptotic cell death. Apoptosis (programmed cell death) plays essential roles in embryonic development and pathogenesis of various diseases, such as degenerative neuronal diseases, cardiovascular diseases and cancer. One of the most commonly studied pathways, which involves kinase regulation of apoptosis, is cellular signaling from growth factor receptors at the cell surface to the nucleus (Crews and Erikson, Cell, 74:215-17, 1993).

Protein tyrosine kinases (PTKs) catalyze the phosphorylation of specific tyrosyl residues in various proteins involved in the regulation of cell growth and differentiation. (A. F. Wilks, Progress in Growth Factor Research, 1990, 2, 97-111; S. A. Courtneidge, Dev. Supp. I, 1993, 57-64; J. A. Cooper, Semin. Cell Biol., 1994, 5(6), 377-387; R. F. Paulson, Semin. Immunol., 1995, 7(4), 267-277; A. C. Chan, Curr. Opin. Immunol., 1996, 8(3), 394-401). Inappropriate or uncontrolled activation of many PTKs, i.e. aberrant PTK activity, for example by over-expression or mutation, has been shown to result in uncontrolled cell growth.

Aberrant protein tyrosine kinase (PTK) activity has been implicated in a variety of disorders including psoriasis, rheumatoid arthritis, bronchitis, as well as cancer. Development of effective treatments for such disorders is a constant and ongoing enterprise in the medical field. The ErbB family of PTKs, which includes ErbB-2, EGFR, ErbB-3 and ErbB-4, is one group of PTKs that has attracted interest as a therapeutic target. Currently, of special interest, is the role of ErbB family PTKs in hyperproliferative disorders, particularly human malignancies. Elevated EGFR activity has, for example, been implicated in non-small cell lung, bladder, and head and neck cancers. Furthermore, increased ErbB-2 activity has been implicated in breast, ovarian, gastric and pancreatic cancers. Overexpression of HRG and/or HER3 has been reported in numerous cancers, including gastric, ovarian, prostate, bladder, and breast tumors and is associated with poor prognosis (B. Tanner, J Clin Oncol. 2006, 24(26):4317-23; M. Hayashi, Clin. Cancer Res. 2008.14(23):7843-9.; H. Kaya, Eur J Gynaecol Oncol. 2008; 29(4):350-6). Consequently, inhibition of ErbB family PTKs should provide a treatment for disorders characterized by aberrant ErbB family PTK activity. The biological role of ErbB family PTKs and their implication in various disease states is discussed, for instance in U.S. Pat. No. 5,773,476; International Patent Application WO 99/35146; M. C. Hung et al, Seminars in Oncology, 26: 4, Suppl. 12 (August) 1999, 51-59; Ullrich et al, Cell, 61: 203-212, Apr. 20, 1990; Modjtahedi et al, Intl J. of Oncology, 13: 335-342, 1998; and J. R. Woodburn, Pharmacol. Ther., 82: 2-3, 241-250, 1999, it is generally accepted that inhibitors of ErbB family kinases will be useful for the treatment of such cancers or other condition associated with ErbB family kinases.

Mitogen-activated protein (MAP) Kinase/extracellular signal-regulated kinase (ERK) kinase (hereinafter referred to as MEK) is known to be involved in the regulation of cell proliferation as a kinase that mediates Raf-MEK-ERK signal transduction pathway, and the Raf family (B-Raf, C-Raf etc.) activates the MEK family (MEK-1, MEK-2 etc.) and the MEK family activates the ERK family (ERK-1 and ERK-2).

Activation of Raf-MEK-ERK signal transduction pathway in cancer, particularly colorectal cancer, pancreatic cancer, lung cancer, breast cancer and the like, has been frequently observed.

In addition, since the signals produced by signal molecules such as growth factor, cytokine and the like converge to the activation of MEK-ERK, inhibitors of these functions are considered to more effectively suppress Raf-MEK-ERK signal transduction than suppression of the function of upstream kinases such as RTK, Ras, and Raf.

Moreover, it is also known that a compound having MEK inhibitory activity effectively induces inhibition of ERK1/2 activity and suppression of cell proliferation (The Journal of Biological Chemistry, vol. 276, No. 4, pp. 2686-2692, 2001), and the compound is expected to show effects on diseases caused by undesirable cell proliferation, such as tumor genesis and/or cancer.

It would be useful to provide a novel therapy which provides more effective and/or enhanced treatment of an individual suffering the effects of cancer.

SUMMARY OF THE INVENTION

One embodiment of this invention provides a combination comprising:
(i) a compound of Structure (I):

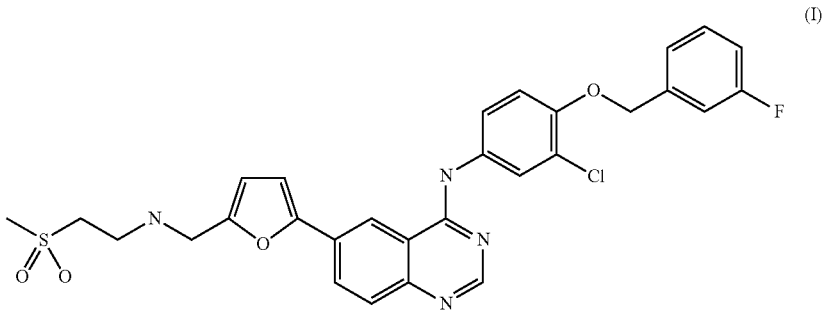

or a pharmaceutically acceptable hydrate and/or salt thereof; and (ii) a compound of Structure (II):

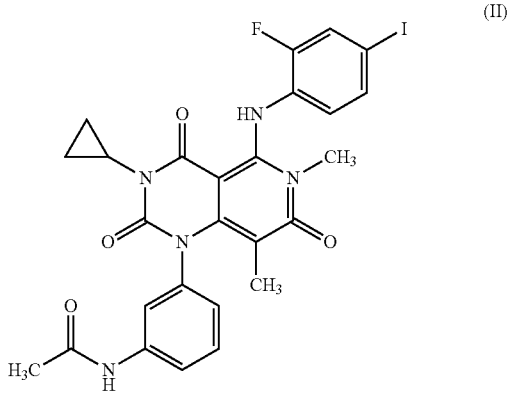

or a pharmaceutically acceptable salt or solvate thereof.

One embodiment of this invention provides a method of treating cancer in a human in need thereof which comprises the in vivo administration of a therapeutically effective amount of a combination of N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate and/or salt thereof, suitably the ditosylate monohydrate salt, thereof, and N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate, suitably the dimethyl sulfoxide solvate, thereof, to such human.

One embodiment of this invention provides a method of treating cancer in a human in need thereof which comprises the in vivo administration of a therapeutically effective amount of a combination of N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate and/or salt thereof, suitably the ditosylate monohydrate salt, thereof, and N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate, suitably the dimethyl sulfoxide solvate, thereof, to such human, wherein the combination is administered within a specified period, and wherein the combination is administered for a duration of time.

One embodiment of this invention provides a method of treating cancer in a human in need thereof which comprises the in vivo administration of a therapeutically effective amount of a combination of N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate and/or salt thereof, suitably the ditosylate monohydrate salt, thereof, and N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate, suitably the dimethyl sulfoxide solvate, thereof, to such human, wherein the compounds of the combination are administered sequentially.

DETAILED DESCRIPTION OF THE INVENTION

Figure 1:
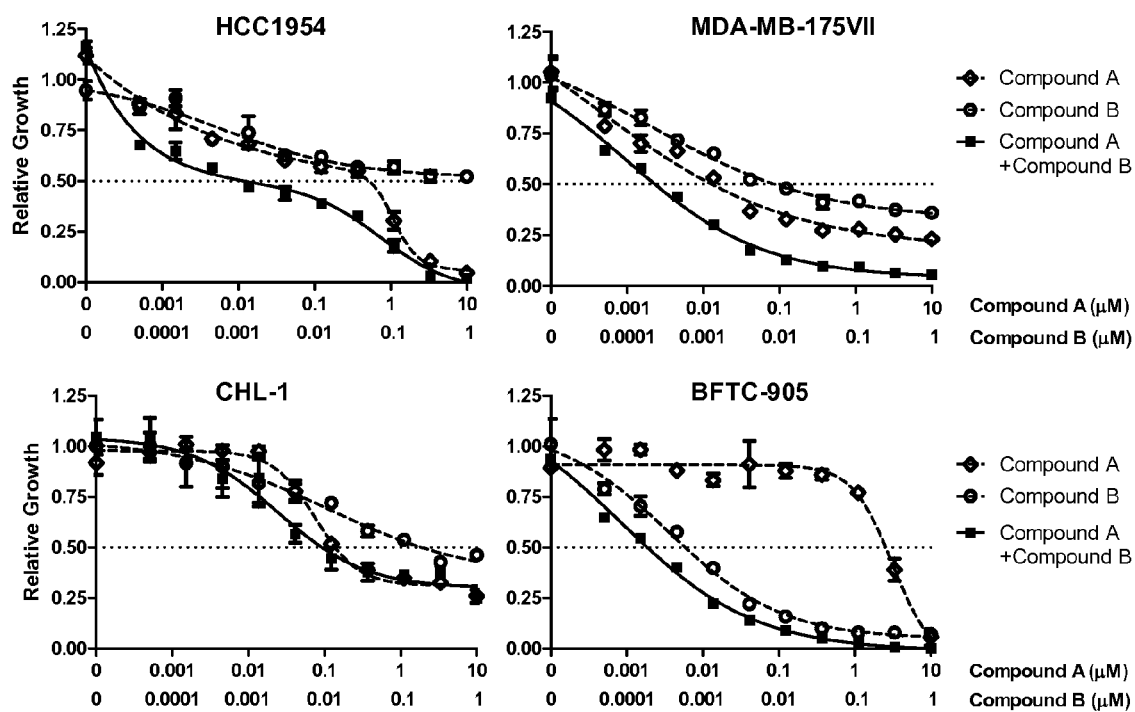
FIG. 1 depicts dose response curves of cell growth inhibition 72 hours post treatment of HCC1954, MDA-MB-175VII, CHL-1 and BFTC-905 cells with Compound A, Compound B or the 10 to 1 molar ratio combination of Compound A and Compound B.

The present invention relates to combinations that exhibit antiproliferative activity. Suitably, the method relates to methods of treating cancer by the co-administration of N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate and/or salt thereof, suitably the ditosylate monohydrate salt, thereof, (hereinafter Compound A, or a pharmaceutically acceptable hydrate and/or salt, suitably the ditosylate monohydrate salt, thereof, which compound is represented by Structure I:

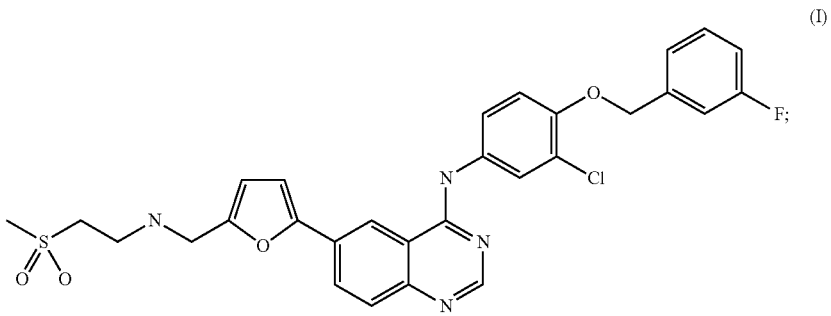

and N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate, suitably the dimethyl sulfoxide solvate, thereof, (hereinafter Compound B or a pharmaceutically acceptable salt or solvate, suitably the dimethyl sulfoxide solvate, thereof, which compound is represented by Structure II:

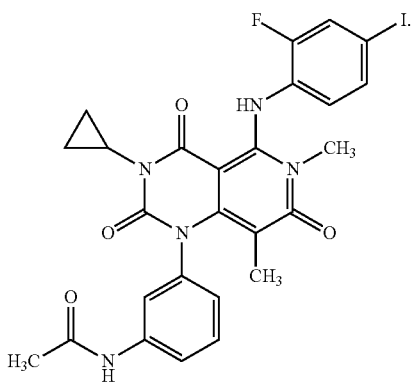

(II)

Compound A is disclosed and claimed, along with pharmaceutically acceptable solvates and salts thereof, as being useful as an inhibitor of EGF-R/erbB-2 activity, particularly in treatment of cancer, in International Application No. PCT/EP99/00048, having an International filing date of Jan. 8, 1999, International Publication Number WO 99/35146 and an International Publication date of Jul. 15, 1999, the entire disclosure of which is hereby incorporated by reference, Compound A is the compound of Example 29. Compound A can be prepared as described in International Application No. PCT/E P99/00048.

Suitably, Compound A is in the form of a ditosylate monohydrate salt. This salt form can be prepared by one of skill in the art from the description in International Application No. PCT/US01/20706, having an International filing date of Jun. 28, 2001, International Publication Number WO 02/02552 and an International Publication date of Jan. 10, 2002, the entire disclosure of which is hereby incorporated by reference, see particularly Example 10.

Suitable pharmaceutical compositions containing Compound A as a single active ingredient are prepared as described in International Application No. PCT/US2006/014447, having an International filing date of Apr. 18, 2006, International Publication Number WO 06/113649 and an International Publication date of Oct. 26, 2006, the entire disclosure of which is hereby incorporated by reference, see particularly the formulation in Table 3.

Compound A is sold commercially as the ditosylate monohydrate salt and is known by the generic name lapatinib and trade names Tykerb® and Tyverb®.

Compound B is disclosed and claimed, along with pharmaceutically acceptable salts and solvates thereof, as being useful as an inhibitor of MEK activity, particularly in treatment of cancer, in International Application No. PCT/JP2005/011082, having an International filing date of Jun. 10, 2005; International Publication Number WO 2005/121142 and an International Publication date of Dec. 22, 2005, the entire disclosure of which is hereby incorporated by reference, Compound B is the compound of Example 4-1. Compound B can be prepared as described in International Application No. PCT/JP2005/011082. Compound B can be prepared as described in United States Patent Publication No. US 2006/0014768, Published Jan. 19, 2006, the entire disclosure of which is hereby incorporated by reference.

Suitably, Compound B is in the form of a dimethyl sulfoxide solvate. Suitably, Compound B is in the form of a sodium salt. Suitably, Compound B is in the form of a solvate selected from: hydrate, acetic acid, ethanol, nitromethane, chlorobenzene, 1-pentanci, isopropyl alcohol, ethylene glycol and 3-methyl-1-butanol. These solvates and salt forms can be prepared by one of skill in the art from the description in International Application No. PCT/JP2005/011082 or United States Patent Publication No. US 2006/0014768.

The administration of a therapeutically effective amount of the combinations of the invention are advantageous over the individual component compounds in that the combinations will provide one or more of the following improved properties when compared to the individual administration of a therapeutically effective amount of a component compound: i) a greater anticancer effect than the most active single agent, ii) synergistic or highly synergistic anticancer activity, iii) a dosing protocol that provides enhanced anticancer activity with reduced side effect profile, iv) a reduction in the toxic effect profile, v) an increase in the therapeutic window, vi) an increase in the bioavailability of one or both of the component compounds, or vii) an increase in apoptosis over the individual component compounds.

The compounds of the invention may contain one or more chiral atoms, or may otherwise be capable of existing as two enantiomers. Accordingly, the compounds of this invention include mixtures of enantiomers as well as purified enantiomers or enantiomerically enriched mixtures. Also, it is understood that all tautomers and mixtures of tautomers are included within the scope of Compound A, and pharmaceutically acceptable hydrates and/or salts thereof, and Compound B, and pharmaceutically acceptable salts or solvates thereof.

The compounds of the invention may form a solvate which is understood to be a complex of variable stoichiometry formed by a solute (in this invention, Compound A or a salt thereof and/or Compound B or a salt thereof) and a solvent. Such solvents for the purpose of the invention may not interfere with the biological activity of the solute. Examples of suitable solvents include, but are not limited to, water, methanol, dimethyl sulfoxide, ethanol and acetic acid. Suitably the solvent used is a pharmaceutically acceptable solvent. Suitably the solvent used is water.

The pharmaceutically acceptable salts of the compounds of the invention are readily prepared by those of skill in the art.

Also, contemplated herein is a method of treating cancer using a combination of the invention where Compound A, or a pharmaceutically acceptable hydrate and/or salt thereof, and/or Compound B or a pharmaceutically acceptable salt or solvate thereof are administered as pro-drugs. Pharmaceutically acceptable pro-drugs of the compounds of the invention are readily prepared by those of skill in the art.

When referring to a dosing protocol, the term "day", "per day" and the like, refer to a time within one calendar day which begins at midnight and ends at the following midnight.

By the term "treating" and derivatives thereof as used herein, is meant therapeutic therapy. In reference to a particular condition, treating means: (1) to ameliorate or prevent the condition of one or more of the biological manifestations of the condition, (2) to interfere with (a) one or more points in the biological cascade that leads to or is responsible for the condition or (b) one or more of the biological manifestations of the condition, (3) to alleviate one or more of the symptoms, effects or side effects associated with the condition or treatment thereof, or (4) to slow the progression of the condition or one or more of the biological manifestations of the condition. Prophylactic therapy is also contemplated thereby. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof. Prophylactic therapy is appropriate, for example, when a subject is considered at high risk for developing cancer, such as when a subject has a strong family history of cancer or when a subject has been exposed to a carcinogen.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

By the term "combination" and derivatives thereof, as used herein is meant either, simultaneous administration or any manner of separate sequential administration of a therapeutically effective amount of Compound A, or a pharmaceutically acceptable hydrate and/or salt thereof, and Compound B or a pharmaceutically acceptable salt or solvate thereof. Preferably, if the administration is not simultaneous, the compounds are administered in a close time proximity to each other. Furthermore, it does not matter if the compounds are administered in the same dosage form, e.g. one compound may be administered topically and the other compound may be administered orally. Suitably, both compounds are administered orally.

By the term "combination kit" as used herein is meant the pharmaceutical composition or compositions that are used to administer Compound A, or a pharmaceutically acceptable hydrate and/or salt thereof, and Compound B, or a pharmaceutically acceptable salt or solvate thereof, according to the invention. When both compounds are administered simultaneously, the combination kit can contain Compound A, or a pharmaceutically acceptable hydrate and/or salt thereof, and Compound B, or a pharmaceutically acceptable salt or solvate thereof, in a single pharmaceutical composition, such as a tablet, or in separate pharmaceutical compositions. When the compounds are not administered simultaneously, the combination kit will contain Compound A, or a pharmaceutically acceptable hydrate and/or salt thereof, and Compound B, or a pharmaceutically acceptable salt or solvate thereof, in separate pharmaceutical compositions. The combination kit can comprise Compound A, or a pharmaceutically acceptable hydrate and/or salt thereof, and Compound B, or a pharmaceutically acceptable salt or solvate thereof, in separate pharmaceutical compositions in a single package or in separate pharmaceutical compositions in separate packages.

In one aspect there is provided a combination kit comprising the components:

Compound A, or a pharmaceutically acceptable hydrate and/or salt thereof, in association with a pharmaceutically acceptable carrier; and Compound B, or a pharmaceutically acceptable salt or solvate thereof, in association with a pharmaceutically acceptable carrier.

In one embodiment of the invention the combination kit comprises the following components:

Compound A, or a pharmaceutically acceptable hydrate and/or salt thereof, in association with a pharmaceutically acceptable carrier; and Compound B, or a pharmaceutically acceptable salt or solvate thereof, in association with a pharmaceutically acceptable carrier, wherein the components are provided in a form which is suitable for sequential, separate and/or simultaneous administration.

In one embodiment the combination kit comprises:

a first container comprising Compound A, or a pharmaceutically acceptable hydrate and/or salt thereof, in association with a pharmaceutically acceptable carrier; and a second container comprising Compound B, or a pharmaceutically acceptable salt or solvate thereof, in association with a pharmaceutically acceptable carrier, and a container means for containing said first and second containers.

The "combination kit" can also be provided by instruction, such as dosage and administration instructions. Such dosage and administration instructions can be of the kind that is provided to a doctor, for example by a drug product label, or they can be of the kind that is provided by a doctor, such as instructions to a patient.

Unless otherwise defined, in all dosing protocols described herein, the regimen of compounds administered does not have to commence with the start of treatment and terminate with the end of treatment, it is only required that the number of consecutive days in which both compounds are administered and the optional number of consecutive days in which only one of the component compounds is administered, or the indicated dosing protocol—including the amount of compound administered, occur at some point during the course of treatment.

As used herein the term "Compound $A^2$" means—Compound A, or a pharmaceutically acceptable hydrate and/or salt thereof—.

As used herein the term "Compound $B^2$" means—Compound B, or a pharmaceutically acceptable salt or solvate thereof—.

The term "loading dose" as used herein will be understood to mean a single dose or short duration regimen of Compound A or Compound B having a dosage higher than the maintenance dose administered to the subject to rapidly increase the blood concentration level of the drug. Suitably, a short duration regimen for use herein will be from: 1 to 14 days; suitably from 1 to 7 days; suitably from 1 to 3 days; suitably for three days; suitably for two days; suitably for one day. In some embodiments, the "loading dose" can increase the blood concentration of the drug to a therapeutically effective level. In some embodiments, the "loading dose" can increase the blood concentration of the drug to a therapeutically effective level in conjunction with a maintenance dose of the drug. The "loading dose" can be administered once per day, or more than once per day (e.g., up to 4 times per day). Suitably the "loading dose" will be administered once a day. Suitably, the loading dose will be an amount from 2 to 100 times the maintenance dose; suitably from 2 to 10 times; suitably from 2 to 5 times; suitably 2 times; suitably 3 times; suitably 4 times; suitably 5 times. Suitably, the loading dose will be administered for from 1 to 7 days; suitably from 1 to 5 days; suitably from 1 to 3 days; suitably for 1 day; suitably for 2 days; suitably for 3 days, followed by a maintenance dosing protocol.

The term "maintenance dose" as used herein will be understood to mean a dose that is serially administered (for example, at least twice), and which is intended to either slowly raise blood concentration levels of the compound to a therapeutically effective level, or to maintain such a therapeutically effective level. The maintenance dose is generally administered once per day and the daily dose of the maintenance dose is lower than the total daily dose of the loading dose.

Suitably the combinations of this invention are administered within a "specified period".

By the term "specified period" and derivatives thereof, as used herein is meant the interval of time between the administration of one of Compound $A^2$ and Compound $B^2$ and the other of Compound $A^2$ and Compound $B^2$. Unless otherwise defined, the specified period can include simultaneous administration. When both compounds of the invention are administered once a day the specified period refers to timing of the administration of Compound $A^2$ and Compound $B^2$ during a single day. When one or both compounds of the invention are administered more than once a day, the specified period is calculated based on the first administration of each compound on a specific day. All administrations of a compound of the invention that are subsequent to the first during a specific day are not considered when calculating the specific period.

Suitably, if the compounds are administered within a "specified period" and not administered simultaneously, they are both administered within about 24 hours of each other—in this case, the specified period will be about 24 hours; suitably they will both be administered within about 12 hours of each other—in this case, the specified period will be about 12 hours; suitably they will both be administered within about 11 hours of each other—in this case, the specified period will be about 11 hours; suitably they will both be administered within about 10 hours of each other—in this case, the specified period will be about 10 hours; suitably they will both be administered within about 9 hours of each other—in this case, the specified period will be about 9 hours; suitably they will both be administered within about 8 hours of each other—in this case, the specified period will be about 8 hours; suitably they will both be administered within about 7 hours of each other—in this case, the specified period will be about 7 hours; suitably they will both be administered within about 6 hours of each other—in this case, the specified period will be about 6 hours; suitably they will both be administered within about 5 hours of each other—in this case, the specified period will be about 5 hours; suitably they will both be administered within about 4 hours of each other—in this case, the specified period will be about 4 hours; suitably they will both be administered within about 3 hours of each other—in this case, the specified period will be about 3 hours; suitably they will be administered within about 2 hours of each other—in this case, the specified period will be about 2 hours; suitably they will both be administered within about 1 hour of each other—in this case, the specified period will be about 1 hour. As used herein, the administration of Compound $A^2$ and Compound $B^2$ in less than about 45 minutes apart is considered simultaneous administration.

Suitably, when the combination of the invention is administered for a "specified period", the compounds will be co-administered for a "duration of time".

By the term "duration of time" and derivatives thereof, as used herein is meant that both compounds of the invention are administered within a "specified period" for an indicated number of consecutive days, optionally followed by a number of consecutive days where only one of the component compounds is administered.

Regarding "specified period" administration:

Suitably, during the course of treatment, both compounds will be administered within a specified period for at least 1 day—in this case, the duration of time will be at least 1 day; suitably, during the course of treatment, both compounds will be administered within a specified period for at least 2 consecutive days—in this case, the duration of time will be at least 2 days; suitably, during the course of treatment, both compounds will be administered within a specified period for at least 3 consecutive days—in this case, the duration of time will be at least 3 days; suitably, during the course of treatment, both compounds will be administered within a specified period for at least 5 consecutive days—in this case, the duration of time will be at least 5 days; suitably, during the course of treatment, both compounds will be administered within a specified period for at least 7 consecutive days—in this case, the duration of time will be at least 7 days; suitably, during the course of treatment, both compounds will be administered within a specified period for at least 14 consecutive days—in this case, the duration of time will be at least 14 days; suitably, during the course of treatment, both compounds will be administered within a specified period for at least 30 consecutive days—in this case, the duration of time will be at least 30 days. When, during the course of treatment, both compounds are administered within a specified period for over 30 days, the treatment is considered chronic treatment and will continue until an altering event, such as a reassessment in cancer status or a change in the condition of the patient, warrants a modification to the protocol.

Further regarding "specified period" administration:

Suitably, during the course of treatment, both compounds will be administered within a specified period for at least 1 day, followed by the administration of Compound $A^2$ alone for at least 1 day—in this case, the duration of time will be at least 2 days; suitably, during the course of treatment, both compounds will be administered within a specified period for at least 1 day, followed by administration of Compound $A^2$ alone for at least 2 days—in this case, the duration of time will be at least 3 days; suitably, during the course of treatment, both compounds will be administered within a specified period for at least 1 day, followed by administration of Compound $A^2$ alone for at least 3 days—in this case, the duration of time will be at least 4 days; suitably, during the course of treatment, both compounds will be administered within a specified period for at least 1 day, followed by administration of Compound $A^2$ alone for at least 4 days—in this case, the duration of time will be at least 5 days; suitably, during the course of treatment, both compounds will be administered within a specified period for at least 1 day, followed by administration of Compound $A^2$ alone for at least 5 days—in this case, the duration of time will be at least 6 days; suitably, during the course of treatment, both compounds will be administered within a specified period for at least 1 day, followed by administration of Compound $A^2$ alone for at least 6 days—in this case, the duration of time will be at least 7 days; suitably, during the course of treatment, both compounds will be administered within a specified period for at least 1 day, followed by administration of Compound $A^2$ alone for at least 7 days—in this case, the duration of time will be at least 8 days; suitably, during the course of treatment, both compounds will be administered within a specified period for at least 2 consecutive days, followed by administration of Compound $A^2$ alone for at least 1 day—in this case, the duration of time will be at least 3 days; suitably, during the course of treatment, both compounds will be administered within a specified period for at least 2 consecutive days, followed by administration of Compound $A^2$ alone for at least 2 consecutive days—in this case, the duration of time will be at least 4 days; suitably, during the course of treatment, both compounds will be administered within a specified period for at least 2 consecutive days, followed by administration of Compound $A^2$ alone for at least 3 consecutive days—in this case, the duration of time will be at least 5 days; suitably, during the course of treatment, both compounds will be administered within a specified period for at least 2 consecutive days, followed by administration of Compound $A^2$ alone for at least 4 consecutive days—in this case, the duration of time will be at least 6 days; suitably, during the course of treatment, both compounds will be administered within a specified period for at least 2 consecutive days, followed by administration of Compound $A^2$ alone for at least 5 consecutive days—in this case, the duration of time will be at least 7 days; suitably, during the course of treatment, both compounds will be administered within a specified period for at least 2 consecutive days, followed by administration of Compound $A^2$ alone for at least 6 consecutive days—in this case, the duration of time will be at least 8 days; suitably, during the course of treatment, both compounds will be administered within a specified period for at least 2 consecutive days, followed by administration of Compound $A^2$ alone for at least 7 consecutive days—in this case, the duration of time will be at least 9 days; suitably, during the course of treatment, both compounds will be administered within a specified period for at least 3 consecutive days, followed by administration of Compound $A^2$ alone for at least 1 day—in this case, the duration of time will be at least 4 days; suitably, during the course of treatment, both compounds will be administered within a specified period for at least 3 consecutive days, followed by administration of Compound $A^2$ alone for at least 2 consecutive days—in this case, the duration of time will be at least 5 days; suitably, during the course of treatment, both compounds will be administered within a specified period for at least 3 consecutive days, followed by administration of Compound $A^2$ alone for at least 3 consecutive days—in this case, the duration of time will be at least 6 days; suitably, during the course of treatment, both compounds will be administered within a specified period for at least 3 consecutive days, followed by administration of Compound $A^2$ alone for at least 4 consecutive days—in this case, the duration of time will be at least 7 days; suitably, during the course of treatment, both compounds will be administered within a specified period for at least 3 consecutive days, followed by administration of Compound $A^2$ alone for at least 5 consecutive days—in this case, the duration of time will be at least 8 days; suitably, during the course of treatment, both compounds will be administered within a specified period for at least 3 consecutive days, followed by administration of Compound $A^2$ alone for at least 6 consecutive days—in this case, the duration of time will be at least 9 days; suitably, during the course of treatment, both compounds will be administered within a specified period for at least 3 consecutive days, followed by administration of Compound $A^2$ alone for at least 7 consecutive days—in this case, the duration of time will be at least 10 days; suitably, during the course of treatment, both compounds will be administered within a specified period for at least 4 consecutive days, followed by administration of Compound $A^2$ alone for at least 1 day—in this case, the duration of time will be at least 5 consecutive days; suitably, during the course of treatment, both compounds will be administered within a specified period for at least 4 consecutive days, followed by administration of Compound $A^2$ alone for at least 2 consecutive days—in this case, the duration of time will be at least 6 consecutive days; suitably, during the course of treatment, both compounds will be administered within a specified period for at least 4 consecutive days, followed by administration of Compound $A^2$ alone for at least 3 consecutive days—in this case, the duration of time will be at least 7 consecutive days; suitably, during the course of treatment, both compounds will be administered within a specified period for at least 4 consecutive days, followed by administration of Compound $A^2$ alone for at least 4 consecutive days—in this case, the duration of time will be at least 8 consecutive days; suitably, during the course of treatment, both compounds will be administered within a specified period for at least 4 consecutive days, followed by administration of Compound $A^2$ alone for at least 7 consecutive days—in this case, the duration of time will be at least 11 consecutive days; suitably, during the course of treatment, both compounds will be administered within a specified period for at least 5 consecutive days, followed by administration of Compound $A^2$ alone for at least 1 day—in this case, the duration of time will be at least 6 consecutive days; suitably, during the course of treatment, both compounds will be administered within a specified period for at least 5 consecutive days, followed by administration of Compound $A^2$ alone for at least 2 consecutive days—in this case, the duration of time will be at least 7 consecutive days; suitably, during the course of treatment, both compounds will be administered within a specified period for at least 5 consecutive days, followed by administration of Compound $A^2$ alone for at least 3 consecutive days—in this case, the duration of time will be at least 8 consecutive days; suitably, during the course of treatment, both compounds will be administered within a specified period for at least 5 consecutive days, followed by administration of Compound $A^2$ alone for at least 4 consecutive days—in this case, the duration of time will be at least 9 consecutive days; suitably, during the course of treatment, both compounds will be administered within a specified period for at least 5 consecutive days, followed by administration of Compound $A^2$ alone for at least 5 consecutive days—in this case, the duration of time will be at least 10 consecutive days; suitably, during the course of treatment, both compounds will be administered within a specified period for at least 7 consecutive days, followed by administration of Compound $A^2$ alone for at least 2 consecutive days—in this case, the duration of time will be at least 9 consecutive days; suitably, during the course of treatment, both compounds will be administered within a specified period for at least 14 consecutive days, followed by administration of Compound $A^2$ alone for at least 7 consecutive days—in this case, the duration of time will be at least 21 consecutive days; suitably, during the course of treatment, both compounds will be administered within a specified period for at least 30 consecutive days, followed by administration of Compound $A^2$ alone for at least 7 consecutive days—in this case, the duration of time will be at least 37 consecutive days. Suitably, during the course of treatment, both compounds will be administered within a specified period for from 1 to 3 consecutive days, followed by administration of Compound $A^2$ alone for from 3 to 7 consecutive days. Suitably, during the course of treatment, both compounds will be administered within a specified period for from 3 to 6 consecutive days, followed by administration of Compound $A^2$ alone for from 1 to 4 consecutive days. Suitably, during the course of treatment, both compounds will be administered within a specified period for 5 consecutive days, followed by administration of Compound $A^2$ alone for 2 consecutive days. Suitably, during the course of treatment, both compounds will be administered within a specified period for 2 consecutive days, followed by administration of Compound $A^2$ alone for from 3 to 7 consecutive days. Suitably, during the course of treatment, both compounds will be administered within a specified period for from 1 to 3 days over a 7 day period, and during the other days of the 7 day period Compound $A^2$ will be administered alone. Suitably, during the course of treatment, both compounds will be administered within a specified period for 2 days over a 7 day period, and during the other days of the 7 day period Compound $A^2$ will be administered alone.

Further regarding "specified period" administration:

Suitably, during the course of treatment, both compounds will be administered within a specified period for at least 1 day, followed by the administration of Compound $B^2$ alone for at least 1 day—in this case, the duration of time will be at least 2 days; suitably, during the course of treatment, both compounds will be administered within a specified period for at least 1 day, followed by administration of Compound $B^2$ alone for at least 2 days—in this case, the duration of time will be at least 3 days; suitably, during the course of treatment, both compounds will be administered within a specified period for at least 1 day, followed by administration of Compound $B^2$ alone for at least 3 days—in this case, the duration of time will be at least 4 days; suitably, during the course of treatment, both compounds will be administered within a specified period for at least 1 day, followed by administration of Compound $B^2$ alone for at least 4 days—in this case, the duration of time will be at least 5 days; suitably, during the course of treatment, both compounds will be administered within a specified period for at least 1 day, followed by administration of Compound $B^2$ alone for at least 5 days—in this case, the duration of time will be at least 6 days; suitably, during the course of treatment, both compounds will be administered within a specified period for at least 1 day, followed by administration of Compound $B^2$ alone for at least 6 days—in this case, the duration of time will be at least 7 days; suitably, during the course of treatment, both compounds will be administered within a specified period for at least 1 day, followed by administration of Compound $B^2$ alone for at least 7 days—in this case, the duration of time will be at least 8 days; suitably, during the course of treatment, both compounds will be administered within a specified period for at least 2 consecutive days, followed by administration of Compound $B^2$ alone for at least 1 day—in this case, the duration of time will be at least 3 days; suitably, during the course of treatment, both compounds will be administered within a specified period for at least 2 consecutive days, followed by administration of Compound $B^2$ alone for at least 2 consecutive days—in this case, the duration of time will be at least 4 days; suitably, during the course of treatment, both compounds will be administered within a specified period for at least 2 consecutive days, followed by administration of Compound $B^2$ alone for at least 3 consecutive days—in this case, the duration of time will be at least 5 days; suitably, during the course of treatment, both compounds will be administered within a specified period for at least 2 consecutive days, followed by administration of Compound $B^2$ alone for at least 4 consecutive days—in this case, the duration of time will be at least 6 days; suitably, during the course of treatment, both compounds will be administered within a specified period for at least 2 consecutive days, followed by administration of Compound $B^2$ alone for at least 5 consecutive days—in this case, the duration of time will be at least 7 days; suitably, during the course of treatment, both compounds will be administered within a specified period for at least 2 consecutive days, followed by administration of Compound $B^2$ alone for at least 6 consecutive days—in this case, the duration of time will be at least 8 days; suitably, during the course of treatment, both compounds will be administered within a specified period for at least 2 consecutive days, followed by administration of Compound $B^2$ alone for at least 7 consecutive days—in this case, the duration of time will be at least 9 days; suitably, during the course of treatment, both compounds will be administered within a specified period for at least 3 consecutive days, followed by administration of Compound $B^2$ alone for at least 1 day—in this case, the duration of time will be at least 4 days; suitably, during the course of treatment, both compounds will be administered within a specified period for at least 3 consecutive days, followed by administration of Compound $B^2$ alone for at least 2 consecutive days—in this case, the duration of time will be at least 5 days; suitably, during the course of treatment, both compounds will be administered within a specified period for at least 3 consecutive days, followed by administration of Compound $B^2$ alone for at least 3 consecutive days—in this case, the duration of time will be at least 6 days; suitably, during the course of treatment, both compounds will be administered within a specified period for at least 3 consecutive days, followed by administration of Compound $B^2$ alone for at least 4 consecutive days—in this case, the duration of time will be at least 7 days; suitably, during the course of treatment, both compounds will be administered within a specified period for at least 3 consecutive days, followed by administration of Compound $B^2$ alone for at least 5 consecutive days—in this case, the duration of time will be at least 8 days; suitably, during the course of treatment, both compounds will be administered within a specified period for at least 3 consecutive days, followed by administration of Compound $B^2$ alone for at least 6 consecutive days—in this case, the duration of time will be at least 9 days; suitably, during the course of treatment, both compounds will be administered within a specified period for at least 3 consecutive days, followed by administration of Compound $B^2$ alone for at least 7 consecutive days—in this case, the duration of time will be at least 10 days; suitably, during the course of treatment, both compounds will be administered within a specified period for at least 4 consecutive days, followed by administration of Compound $B^2$ alone for at least 1 day—in this case, the duration of time will be at least 5 consecutive days; suitably, during the course of treatment, both compounds will be administered within a specified period for at least 4 consecutive days, followed by administration of Compound $B^2$ alone for at least 2 consecutive days—in this case, the duration of time will be at least 6 consecutive days; suitably, during the course of treatment, both compounds will be administered within a specified period for at least 4 consecutive days, followed by administration of Compound $B^2$ alone for at least 3 consecutive days—in this case, the duration of time will be at least 7 consecutive days; suitably, during the course of treatment, both compounds will be administered within a specified period for at least 4 consecutive days, followed by administration of Compound $B^2$ alone for at least 4 consecutive days—in this case, the duration of time will be at least 8 consecutive days; suitably, during the course of treatment, both compounds will be administered within a specified period for at least 4 consecutive days, followed by administration of Compound $B^2$ alone for at least 7 consecutive days—in this case, the duration of time will be at least 11 consecutive days; suitably, during the course of treatment, both compounds will be administered within a specified period for at least 5 consecutive days, followed by administration of Compound $B^2$ alone for at least 1 day—in this case, the duration of time will be at least 6 consecutive days; suitably, during the course of treatment, both compounds will be administered within a specified period for at least 5 consecutive days, followed by administration of Compound $B^2$ alone for at least 2 consecutive days—in this case, the duration of time will be at least 7 consecutive days; suitably, during the course of treatment, both compounds will be administered within a specified period for at least 5 consecutive days, followed by administration of Compound $B^2$ alone for at least 3 consecutive days—in this case, the duration of time will be at least 8 consecutive days; suitably, during the course of treatment, both compounds will be administered within a specified period for at least 5 consecutive days, followed by administration of Compound $B^2$ alone for at least 4 consecutive days—in this case, the duration of time will be at least 9 consecutive days; suitably, during the course of treatment, both compounds will be administered within a specified period for at least 5 consecutive days, followed by administration of Compound $B^2$ alone for at least 5 consecutive days—in this case, the duration of time will be at least 10 consecutive days; suitably, during the course of treatment, both compounds will be administered within a specified period for at least 7 consecutive days, followed by administration of Compound $B^2$ alone for at least 2 consecutive days—in this case, the duration of time will be at least 9 consecutive days; suitably, during the course of treatment, both compounds will be administered within a specified period for at least 14 consecutive days, followed by administration of Compound $B^2$ alone for at least 7 consecutive days—in this case, the duration of time will be at least 21 consecutive days; suitably, during the course of treatment, both compounds will be administered within a specified period for at least 30 consecutive days, followed by administration of Compound $B^2$ alone for at least 7 consecutive days—in this case, the duration of time will be at least 37 consecutive days. Suitably, during the course of treatment, both compounds will be administered within a specified period for from 1 to 3 consecutive days, followed by administration of Compound $B^2$ alone for from 3 to 7 consecutive days. Suitably, during the course of treatment, both compounds will be administered within a specified period for from 3 to 6 consecutive days, followed by administration of Compound $B^2$ alone for from 1 to 4 consecutive days. Suitably, during the course of treatment, both compounds will be administered within a specified period for 5 consecutive days, followed by administration of Compound $B^2$ alone for 2 consecutive days. Suitably, during the course of treatment, both compounds will be administered within a specified period for 2 consecutive days, followed by administration of Compound $B^2$ alone for from 3 to 7 consecutive days. Suitably, during the course of treatment, both compounds will be administered within a specified period for from 1 to 3 days over a 7 day period, and during the other days of the 7 day period Compound $B^2$ will be administered alone. Suitably, during the course of treatment, both compounds will be administered within a specified period for 2 days over a 7 day period, and during the other days of the 7 day period Compound $B^2$ will be administered alone.

Further regarding "specified period" administration:

Suitably, during the course of treatment, Compound $A^2$ and Compound $B^2$ will be administered within a specified period for from 1 to 3 days over a 7 day period, and during the other days of the 7 day period Compound $A^2$ will be administered alone. Suitably, this 7 day protocol is repeated for 2 cycles or for 14 days; suitably for 4 cycles or 28 days; suitably for continuous administration.

Suitably, during the course of treatment, Compound $A^2$ and Compound $B^2$ will be administered within a specified period for from 1 to 3 days over a 7 day period, and during the other days of the 7 day period Compound $B^2$ will be administered alone. Suitably, this 7 day protocol is repeated for 2 cycles or for 14 days; suitably for 4 cycles or 28 days; suitably for continuous administration.

Suitably, during the course of treatment, Compound $A^2$ and Compound $B^2$ will be administered within a specified period for 3 days over a 7 day period, and during the other days of the 7 day period Compound $A^2$ will be administered alone. Suitably, this 7 day protocol is repeated for 2 cycles or for 14 days; suitably for 4 cycles or 28 days; suitably for continuous administration.

Suitably, during the course of treatment, Compound $A^2$ and Compound $B^2$ will be administered within a specified period for 3 days over a 7 day period, and during the other days of the 7 day period Compound $B^2$ will be administered alone. Suitably, this 7 day protocol is repeated for 2 cycles or for 14 days; suitably for 4 cycles or 28 days; suitably for continuous administration.

Suitably, during the course of treatment, Compound $A^2$ and Compound $B^2$ will be administered within a specified period for 2 days over a 7 day period, and during the other days of the 7 day period Compound $A^2$ will be administered alone. Suitably, this 7 day protocol is repeated for 2 cycles or for 14 days; suitably for 4 cycles or 28 days; suitably for continuous administration.

Suitably, during the course of treatment, Compound $A^2$ and Compound $B^2$ will be administered within a specified period for 2 days over a 7 day period, and during the other days of the 7 day period Compound $B^2$ will be administered alone. Suitably, this 7 day protocol is repeated for 2 cycles or for 14 days; suitably for 4 cycles or 28 days; suitably for continuous administration.

Suitably, during the course of treatment, Compound $A^2$ and Compound $B^2$ will be administered within a specified period for 1 day during a 7 day period, and during the other days of the 7 day period Compound $A^2$ will be administered alone. Suitably, this 7 day protocol is repeated for 2 cycles or for 14 days; suitably for 4 cycles or 28 days; suitably for continuous administration.

Suitably, during the course of treatment, Compound $A^2$ and Compound $B^2$ will be administered within a specified period for 1 day during a 7 day period, and during the other days of the 7 day period Compound $B^2$ will be administered alone. Suitably, this 7 day protocol is repeated for 2 cycles or for 14 days; suitably for 4 cycles or 28 days; suitably for continuous administration.

Suitably, during the course of treatment, Compound $A^2$ and Compound $B^2$ will be administered within a specified period for from 1 to 5 days over a 14 day period, and during the other days of the 14 day period Compound $A^2$ will be administered alone. Suitably, this 14 day protocol is repeated for 2 cycles or for 28 days; suitably for continuous administration.

Suitably, during the course of treatment, Compound $A^2$ and Compound $B^2$ will be administered within a specified period for from 1 to 5 days over a 14 day period, and during the other days of the 14 day period Compound $B^2$ will be administered alone. Suitably, this 14 day protocol is repeated for 2 cycles or for 28 days; suitably for continuous administration.

Suitably, if the compounds are not administered during a "specified period", they are administered sequentially. By the term "sequential administration", and derivates thereof, as used herein is meant that one of Compound $A^2$ and Compound $B^2$ is administered for 1 or more consecutive days and the other of Compound $A^2$ and Compound $B^2$ is subsequently administered for 1 or more consecutive days. Unless otherwise defined, the "sequential administration" and in all dosing protocols described herein, do not have to commence with the start of treatment and terminate with the end of treatment, it is only required that the administration of one of Compound $A^2$ and Compound $B^2$ followed by the administration of the other of Compound $A^2$ and Compound $B^2$, or the indicated dosing protocol, occur at some point during the course of treatment. Also, contemplated herein is a drug holiday utilized between the sequential administration of one of Compound $A^2$ and Compound $B^2$ and the other of Compound $A^2$ and Compound $B^2$. As used herein, a drug holiday is a period of days after the sequential administration of one of Compound $A^2$ and Compound $B^2$ and before the administration of the other of Compound $A^2$ and Compound $B^2$ where neither Compound $A^2$ nor Compound $B^2$ is administered. Suitably the drug holiday will be a period of days selected from: 1 day, 2 days, 3 days, 4 days, 5 days, 6 days, 7 days, 8 days, 9 days, 10 days, 11 days, 12 days, 13 days and 14 days.

Regarding Sequential Administration:

Suitably, one of Compound $A^2$ and Compound $B^2$ is administered for from 1 to 30 consecutive days, followed by an optional drug holiday, followed by administration of the other of Compound $A^2$ and Compound $B^2$ for from 1 to 30 consecutive days. Suitably, one of Compound $A^2$ and Compound $B^2$ is administered for from 1 to 21 consecutive days, followed by an optional drug holiday, followed by administration of the other of Compound $A^2$ and Compound $B^2$ for from 1 to 21 consecutive days. Suitably, one of Compound $A^2$ and Compound $B^2$ is administered for from 1 to 14 consecutive days, followed by a drug holiday of from 1 to 14 days, followed by administration of the other of Compound $A^2$ and Compound $B^2$ for from 1 to 14 consecutive days. Suitably, one of Compound $A^2$ and Compound $B^2$ is administered for from 2 to 7 consecutive days, followed by a drug holiday of from 2 to 10 days, followed by administration of the other of Compound $A^2$ and Compound $B^2$ for from 2 to 7 consecutive days.

Suitably, Compound $B^2$ will be administered first in the sequence, followed by an optional drug holiday, followed by administration of Compound $A^2$. Suitably, Compound $B^2$ is administered for from 1 to 21 consecutive days, followed by an optional drug holiday, followed by administration of Compound $A^2$ for from 1 to 21 consecutive days. Suitably, Compound $B^2$ is administered for from 3 to 21 consecutive days, followed by a drug holiday of from 1 to 14 days, followed by administration of Compound $A^2$ for from 3 to 21 consecutive days. Suitably, Compound $B^2$ is administered for from 3 to 21 consecutive days, followed by a drug holiday of from 3 to 14 days, followed by administration of Compound $A^2$ for from 3 to 21 consecutive days. Suitably, Compound $B^2$ is administered for 21 consecutive days, followed by an optional drug holiday, followed by administration of Compound $A^2$ for 14 consecutive days. Suitably, Compound $B^2$ is administered for 14 consecutive days, followed by a drug holiday of from 1 to 14 days, followed by administration of Compound $A^2$ for 14 consecutive days. Suitably, Compound $B^2$ is administered for 7 consecutive days, followed by a drug holiday of from 3 to 10 days, followed by administration of Compound $A^2$ for 7 consecutive days. Suitably, Compound $B^2$ is administered for 3 consecutive days, followed by a drug holiday of from 3 to 14 days, followed by administration of Compound $A^2$ for 7 consecutive days. Suitably, Compound $B^2$ is administered for 3 consecutive days, followed by a drug holiday of from 3 to 10 days, followed by administration of Compound $A^2$ for 3 consecutive days.

Suitably, Compound $A^2$ will be administered first in the sequence, followed by an optional drug holiday, followed by administration of Compound $B^2$. Suitably, Compound $A^2$ is administered for from 1 to 21 consecutive days, followed by an optional drug holiday, followed by administration of Compound $B^2$ for from 1 to 21 consecutive days. Suitably, Compound $A^2$ is administered for from 3 to 21 consecutive days, followed by a drug holiday of from 1 to 14 days, followed by administration of Compound $B^2$ for from 3 to 21 consecutive days. Suitably, Compound $A^2$ is administered for from 3 to 21 consecutive days, followed by a drug holiday of from 3 to 14 days, followed by administration of Compound $B^2$ for from 3 to 21 consecutive days. Suitably, Compound $A^2$ is administered for 21 consecutive days, followed by an optional drug holiday, followed by administration of Compound $B^2$ for 14 consecutive days. Suitably, Compound $A^2$ is administered for 14 consecutive days, followed by a drug holiday of from 1 to 14 days, followed by administration of Compound $B^2$ for 14 consecutive days. Suitably, Compound $A^2$ is administered for 7 consecutive days, followed by a drug holiday of from 3 to 10 days, followed by administration of Compound $B^2$ for 7 consecutive days. Suitably, Compound $A^2$ is administered for 3 consecutive days, followed by a drug holiday of from 3 to 14 days, followed by administration of Compound $B^2$ for 7 consecutive days. Suitably, Compound $A^2$ is administered for 3 consecutive days, followed by a drug holiday of from 3 to 10 days, followed by administration of Compound $B^2$ for 3 consecutive days. Suitably, Compound $A^2$ is administered for 7 consecutive days, followed by administration of Compound $B^2$ for 1 day. Suitably, Compound $A^2$ is administered for 6 consecutive days, followed by administration of Compound $B^2$ for 1 day. Suitably, Compound $B^2$ is administered for 1 day, followed by administration of Compound $A^2$ for 7 consecutive days. Suitably, Compound $B^2$ is administered for 1 day, followed by administration of Compound $A^2$ for 6 consecutive days.

It is understood that a "specified period" administration and a "sequential" administration can be followed by one or more cycles of repeat dosing or can be followed by an alternate dosing protocol, and a drug holiday may precede the repeat dosing or alternate dosing protocol.

Suitably, the amount of Compound $A^2$ administered as part of the combination according to the present invention will be an amount selected from about 250 mg to about 1,500 mg; suitably, the amount will be selected from about 500 mg to about 1,250 mg; suitably, the amount will be selected from about 750 mg to about 1,250 mg; suitably, the amount will be selected from about 1,000 mg to about 1,250 mg; suitably, the amount will be 250 mg, suitably, the amount will be 500 mg, suitably, the amount will be 750 mg, suitably, the amount will be 1,000 mg, suitably, the amount will be 1,250 mg; suitably, the amount will be 1,500 mg. Accordingly, the amount of Compound $A^2$ administered as part of the combination according to the present invention will be an amount selected from about 250 mg to about 1,500 mg. For example, the amount of Compound $A^2$ administered as part of the combination according to the present invention is suitably selected from 250 mg, 500 mg, 750 mg, 1,000 mg, 1,250 mg and 1,500 mg. Suitably, the selected amount of Compound $A^2$ is administered from 1 to 4 times a day, in one or more tablets. Suitably, the selected amount of Compound $A^2$ is administered twice a day, in one or more tablets. Suitably, the selected amount of Compound $A^2$ is administered once a day, in one or more tablets. Suitably, the administration of Compound $A^2$ will begin as a loading dose. Suitably, the loading dose will be an amount from 2 to 100 times the maintenance dose; suitably from 2 to 10 times; suitably from 2 to 5 times; suitably 2 times; suitably 3 times; suitably 4 times; suitably 5 times. Suitably, the loading does will be administered from 1 to 7 days; suitably from 1 to 5 days; suitably from 1 to 3 days; suitably for 1 day; suitably for 2 days; suitably for 3 days, followed by a maintenance dosing protocol.

Suitably, the amount of Compound $B^2$ administered as part of the combination according to the present invention will be an amount selected from about 0.125 mg to about 10 mg; suitably, the amount will be selected from about 0.25 mg to about 9 mg; suitably, the amount will be selected from about 0.25 mg to about 8 mg; suitably, the amount will be selected from about 0.5 mg to about 8 mg; suitably, the amount will be selected from about 0.5 mg to about 7 mg; suitably, the amount will be selected from about 1 mg to about 7 mg; suitably, the amount will be about 5 mg. Accordingly, the amount of Compound A administered as part of the combination according to the present invention will be an amount selected from about 0.125 mg to about 10 mg. For example, the amount of Compound $B^2$ administered as part of the combination according to the present invention can be 0.125 mg, 0.25 mg, 0.5 mg, 0.75 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg. Suitably, the selected amount of Compound $B^2$ is administered from 1 to 4 times a day. Suitably, the selected amount of Compound $B^2$ is administered twice a day. Suitably, the selected amount of Compound $B^2$ is administered once a day. Suitably, the administration of Compound $B^2$ will begin as a loading dose. Suitably, the loading dose will be an amount from 2 to 100 times the maintenance dose; suitably from 2 to 10 times; suitably from 2 to 5 times; suitably 2 times; suitably 3 times; suitably 4 times; suitably 5 times. Suitably, the loading does will be administered from 1 to 7 days; suitably from 1 to 5 days; suitably from 1 to 3 days; suitably for 1 day; suitably for 2 days; suitably for 3 days, followed by a maintenance dosing protocol.

As used herein, all amounts specified for Compound $A^2$ and Compound $B^2$ are indicated as the administered amount of free or unsalted and unsolvated compound per dose.

The method of the present invention may also be employed with other therapeutic methods of cancer treatment.

While it is possible that, for use in therapy, therapeutically effective amounts of the combinations of the present invention may be administered as the raw chemical, it is preferable to present the combinations as a pharmaceutical composition or compositions.

Accordingly, the invention further provides pharmaceutical compositions, which include Compound $A^2$ and/or Compound $B^2$, and one or more pharmaceutically acceptable carriers. The combinations of the present invention are as described above. The carrier(s) must be acceptable in the sense of being compatible with the other ingredients of the formulation, capable of pharmaceutical formulation, and not deleterious to the recipient thereof. In accordance with another aspect of the invention there is also provided a process for the preparation of a pharmaceutical formulation including admixing Compound $A^2$ and/or Compound $B^2$ with one or more pharmaceutically acceptable carriers. As indicated above, such elements of the pharmaceutical combination utilized may be presented in separate pharmaceutical compositions or formulated together in one pharmaceutical formulation.

Pharmaceutical formulations may be presented in unit dose forms containing a predetermined amount of active ingredient per unit dose. As is known to those skilled in the art, the amount of active ingredient per dose will depend on the condition being treated, the route of administration and the age, weight and condition of the patient. Preferred unit dosage formulations are those containing a daily dose or sub-dose, or an appropriate fraction thereof, of an active ingredient. Furthermore, such pharmaceutical formulations may be prepared by any of the methods well known in the pharmacy art.

Compound $A^2$ and Compound $B^2$ may be administered by any appropriate route. Suitable routes include oral, rectal, nasal, topical (including buccal and sublingual), vaginal, and parenteral (including subcutaneous, intramuscular, intravenous, intradermal, intrathecal, and epidural). It will be appreciated that the preferred route may vary with, for example, the condition of the recipient of the combination and the cancer to be treated. It will also be appreciated that each of the agents administered may be administered by the same or different routes and that Compound $A^2$ and Compound $B^2$ may be compounded together in a pharmaceutical composition/formulation. Suitably, Compound $A^2$ and Compound $B^2$ are administered in separate pharmaceutical compositions.

The compounds or combinations of the current invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier may include a prolonged release material, such as glyceryl monostearate or glyceryl distearate, alone or with a wax. The amount of solid carrier varies widely but, suitably, may be from about 25 mg to about 1 g per dosage unit. When a liquid carrier is used, the preparation will suitably be in the form of a syrup, elixir, emulsion, soft gelatin capsule, sterile injectable liquid such as an ampoule, or an aqueous or nonaqueous liquid suspension.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

It should be understood that in addition to the ingredients mentioned above, the formulations may include other agents conventional in the art having regard to the type of formulation in question, for example those suitable for oral administration may include flavoring agents.

As indicated, therapeutically effective amounts of the combinations of the invention (Compound $A^2$ in combination with Compound $B^2$) are administered to a human. Typically, the therapeutically effective amount of the administered agents of the present invention will depend upon a number of factors including, for example, the age and weight of the subject, the precise condition requiring treatment, the severity of the condition, the nature of the formulation, and the route of administration. Ultimately, the therapeutically effective amount will be at the discretion of the attending physician.

The combinations of the invention are tested for efficacy, advantageous and synergistic properties generally according to known procedures.

Suitably, the combinations of the invention are tested for efficacy, advantageous and synergistic properties generally according to the following combination cell proliferation and apoptosis assays.

In Vitro Cell Growth Inhibition by Compound A, Compound B and their Combination in Tumor Cell Lines Methods:

Cell Lines and Growth Conditions

Human tumor cell lines from breast cancer, AU565, BT474, COLO824, HCC1419, HCC1954, HCC2218, JIMT1, MDA-MB-175VII, MDA-MB-453, SK-BR-3 and SUM149, colorectal cancer, LS174T, NCI-H508, NCI-H747, SW403 and T84, melanoma, A375S2, CHL-1 and SK-MEL-5; pancreatic cancer, Capan-1, HPAF-11 and SUIT2, and bladder cancer, 647V, BFTC-905 and SW780 were cultured in RPMI 1640 media containing 10% FBS; BT-474-J4, a breast cancer cell line acquired resistance to Compound A was cultured in RPMI 1640 media containing 10% FBS and 1 µM Compound A. KPL4 breast cancer line was cultured in DMEM containing 5% FBS. All lines were kept in a humidified incubator at 37° C. in 95% air and 5% $CO_2$. JIMT-1 is a cell line established from a tumor of a patient with trastuzumab-resistant breast cancer (Tanner et al, Mol Cancer Ther 2004; 3:1585-92). BT-474-J4 is a single cell clone derived from a culture of BT-474 cells that were selected to grow in the presence of Compound A to a concentration of 3 µM.

Cell Growth Inhibition Assay and Combination Data Analysis.

All cells were cultured for a minimum of 72 hours prior to cell plating. Cells were seeded in a 96-well tissue culture plate (NUNC 136102) of RPMI media containing 10% FBS for all cell lines at 2,000 cells per well except KPL4, which was plated in DMEM containing 5% FBS at 500 cells per well. Approximately 24 hours after plating, cells were exposed to ten, two-fold or three-fold serial dilutions of compound or the combination of the two agents at a constant molar to molar ratio of 10:1 Compound A to Compound B in RPMI media containing 10% FBS or DMEM containing 5% FBS at 500 cells per well for KPL4. Cells were incubated in the presence of compounds for 3 days. ATP levels were determined by adding Cell Titer Glo® reagent (Promega) according to the manufacturer's protocol. Briefly, Cell Titer Glo® reagent was added to each plate, incubated for 20 minutes then the luminescent signal was read on the SpectraMax L plate reader with a 0.5 sec integration time.

Inhibition of cell growth was estimated after treatment with compound or a combination of compounds for three days and comparing the signal to cells treated with vehicle (DMSO). Cell growth was calculated relative to vehicle (DMSO) treated control wells. A concentration of the compound that inhibits 50% of control cell growth ($IC_{50}$) was interpolated using nonlinear regression with the equation, $y=(A+(B-A)/(1+(C/x)^D))$, where A is the minimum response ($y_{min}$), B is the maximum response ($y_{max}$), C is the inflection point of the curve ($EC_{50}$) and D is the Hill coefficient.

Combination effects on potency were evaluated using Combination Index (CI) which was calculated with the back-interpolated $IC_{50}$ values and the mutually non-exclusive equation derived by Chou and Talalay (Chou T C, Talalay P. Quantitative analysis of dose-effect relationships: the combined effects of multiple drugs or enzyme inhibitors. Adv Enzyme Regul 1984; 22:27-55):

$$CI = Da/IC_{50}(a) + Db/IC_{50}(b) + (Da \times Db)/(IC_{50}(a) \times IC_{50}(b))$$

where $IC_{50}(a)$ is the $IC_{50}$ of the inhibitor A; $IC_{50}(b)$ is the $IC_{50}$ for the inhibitor B; Da is the concentration of the inhibitor A in combination with the inhibitor B that inhibited 50% of cell growth; and Db is the concentration of inhibitor B in combination with the inhibitor A that inhibited 50% of cell growth. In general, a CI value <0.9, between 0.9 and 1.1, or >1.1 indicates synergy, additivity and antagonism, respectively. In general, the smaller the CI number, the greater is the strength of synergy.

The combination effects on the response scale were quantified by Excess Over Highest Single Agent (EOHSA) [Liu et al. Mol Cancer Ther. 2011; 10:518-30]. EOHSA values were defined as increases in improvement (here, in 'percentage points' (ppts) difference) produced by the combination over the best single agent at its component dose level for the combination. For single agent and combination treatments, cells were exposed to compounds at a fixed-dose-ratio, and dose response curves were fit to the experimental data and analyzed using regression models described above. At specified total dose levels of $IC_{50}$ along the dose response curve, the corresponding component dose levels for each single agent were calculated. EOHSA was determined by the difference between the response value from the combination (50% inhibition) and the greater response value from the two single agents at the corresponding component dose levels.

Cell Apoptosis Assay-DNA Fragmentation

For investigation of the induction of apoptosis, cells were plated at 5,000 cells per well in a 96-well tissue culture plate and allowed to attach for approximately 24 hours. Forty-eight hours after treatment with compounds, levels of apoptosis were estimated using the Roche Cell Death ELISA kit (Cat. No. 11 774 425 001) following the instructions provided by the manufacturer.

FIG. 1. Dose response curves of cell growth inhibition in HCC1954, MDA-MB-175VII, CHL1 and BFTC-905. Cell growth was determined as described in the method 72 hours post treatment of cells with Compound A, Compound B or the 10 to 1 molar ratio combination of Compound A and Compound B.

Figure 2:
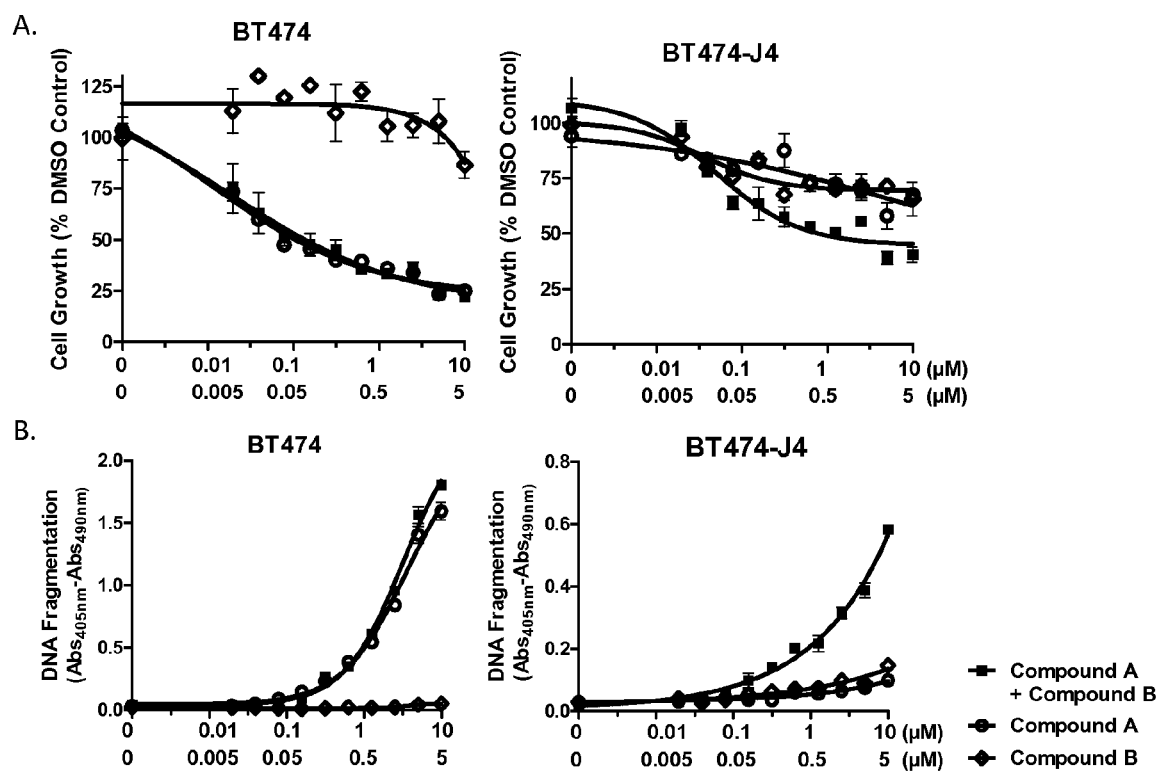
FIG. 2 depicts dose response curves of cell growth inhibition (A) and apoptosis induction (B) in BT474 and BT474-J4 cells determined 72 and 48 hours post treatment with Compound A, Compound B or the 2 to 1 molar ratio combination of Compound A and Compound B respectively.

FIG. 2. Dose response curves of cell growth inhibition (A) and apoptosis induction (B) in BT474 and BT474-J4 cells treated with Compound A, Compound B or the 2 to 1 molar ratio combination of Compound A and Compound B.

Results:

As used in the specification and the "results section", Compound A is N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate and/or salt thereof; Compound B is N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof.

Cell Growth Inhibition by Compound A, Compound B and the Combination of Compound A with Compound B.

The effects of cell growth inhibition by Compound A, Compound B and their combination were determined in ten HER2 positive (HER2+) breast tumor lines, HCC2218, HCC1419, AU565, BT474, SK-BR-3, KPL-4, HCC1954, MDA-MB-453, JIMT-1 and BT474-J4, three HER2 negative (HER2−) breast tumor lines, COLO824, SUM149 and MDA-MB-175VII, five colorectal cancer cell lines, NCI-H747, SW403, NCI-H508, T84 and LS174T, three melanoma cell lines, A375S2, SK-MEL-5 and CHL-1, three pancreatic cancer lines, HPAF-11, Capan-1 and SUIT2, and three bladder cancer lines, BFTC-905, SW780 and 647V. The mean $IC_{50}$s (from at least two independent experiments) and the combination effects at $IC_{50}$s are summarized in Table 1. Representative dose response curves for HCC1954, MDA-MB-175VII, CHL-1 and BFTC-905 are provided in FIG. 1, and for BT474 and BT474-J4 cell lines in FIG. 2A.

For the breast cancer cell lines listed in Table 1, the HER2+ lines were insensitive to Compound B as a single agent ($IC_{50}$>1 µM). The combination of Compound A and Compound B showed cell growth inhibition similar to that of Compound A in HCC2218, HCC1419, AU565, BT474, SK-BR-3 and KPL-4 HER2+ lines, all of which were sensitive to Compound A ($IC_{50}$<1 µM). This combination enhanced the inhibition of cell growth (EOHSA=10-22 ppts) in HCC1954, MDA-MB-453 and BT474-J4 HER2+ lines, which were less sensitive to or resistant to Compound A as single agent. JIMT-1 HER2+ breast cancer line was resistant to Compound A, Compound B or the combination of Compounds A and B. In contrast, the three HER2− breast lines, MDA-MB-175VII, SUM149 and COLO824, were sensitive to Compound B alone ($IC_{50}$≤133 µM). The combination of Compound A and Compound B was synergistic with CI values of 0.38 and 0.51 and enhanced the inhibition of cell growth with EOHSA values of 13 and 17 ppts, respectively in SUM149 and MDA-MB-17511 lines. The combination of Compound A and Compound B showed cell growth inhibition similar to that of Compound B in COLO824, which was highly sensitive to cell growth inhibition by Compound A alone ($IC_{50}$=0.009 μM).

The five colorectal cancer cell lines listed in Table 1 displayed sensitivity to Compound A with $IC_{50}$ values between 0.149 μM and 7.18 μM, and to Compound B with $IC_{50}$ values between 0.003 μM and 0.099 μM. The combination of Compound A and Compound B was synergistic with CI values from 0.25 to 0.70 in all these lines, and enhanced the inhibition of cell growth with EOHSA values from 16 to 31 ppts in three out of the five lines.

For the melanoma cancer cell lines listed in Table 1, the combination of Compound A and Compound B was synergistic with CI value of 0.65 and enhanced the inhibition of cell growth with EOHSA value of 11 ppts in CHL line. This combination had a moderate synergism (CI=0.80) in SK-MEL-5 line, and enhanced the inhibition of cell growth (EOHSA=49) in A375S2 cell line, both of which were highly sensitive to Compound B ($IC_{50}$≤0.003 μM).

The three pancreatic cancer cell lines (Table 1), HPAF-11, Capan-1 and SUIT2, were sensitive to Compound B, however were resistant to Compound A as single agents. The combination of Compound A and Compound B was synergistic in HPAF-11 line (CI=0.5), and enhanced the inhibition of cell growth in HPAF-11 and Capan-1 (EOHSA=10-16 ppts).

For the bladder cancer cell lines listed in Table 1, the combination of Compound A and Compound B was synergistic (CI=0.30) and enhanced the inhibition of cell growth (EOHSA=24 ppts) in BFTC-905 line. This combination was slightly synergistic in SW780 line (CI=0.87) and showed little additional benefit in 647V line.

Cell Apoptosis Induction by Compound A, Compound B and their Combination in Tumor Cell Lines Two HER2+ breast cell lines, BT474 and BT474-J4 were further evaluated for the ability of Compound A, Compound B or the combination of Compound A and Compound B to induce apoptosis determined by DNA fragmentation. DNA fragmentation is a hallmark of induction of apoptosis. Representative DNA fragmentation curves for BT474 and BT474-J4 cells are provided in FIG. 2B. Compound A alone induced apoptosis in BT474, but not in BT474-J4 cells as a single agent. Compound B was not active to induce apoptosis in both lines. However the combination of Compound A and Compound B induced the apoptosis in both BT474 and BT474-J4 cell lines.

TABLE 1

Cell growth inhibition by Compound A, Compound B and their combination in tumor cell lines.

|   | Cancer Cell Lines | Gene Status RAS/RAF/ PIK3CA | Single agent $IC_{50}$ (μM), mean ± STD | | Combination $IC_{50}$ (μM), mean ± STD | | Combination Effects at $IC_{50}$ | |
|---|---|---|---|---|---|---|---|---|
|   |   |   | Compound A | Compound B | Compound A | Compound B | CI, mean ± STD | EOHSA (ppts), mean ± STD |
| I | HCC2218 | WT | 0.031 ± 0.001 | >1 | 0.032 ± 0.006 | 0.003 ± 0.001 | N/A | −0.4 ± 5.4 |
|   | HCC1419 | WT | 0.061 ± 0.053 | >1 | 0.067 ± 0.058 | 0.007 ± 0.006 | N/A | −0.2 ± 3.8 |
|   | AU565 | WT | 0.116 ± 0.006 | >1 | 0.181 ± 0.001 | 0.018 ± 0.000 | N/A | −6.4 ± 1.99 |
|   | BT474 | $PIK3CA^{K111N}$ | 0.144 ± 0.008 | >1 | 0.192 ± 0.082 | 0.019 ± 0.008 | N/A | −2.4 ± 4.4 |
|   | SKBR3 | WT | 0.146 ± 0.047 | >1 | 0.192 ± 0.010 | 0.019 ± 0.001 | N/A | −4.1 ± 4.4 |
|   | KPL4 | $PIK3CA^{H1047R}$ | 0.568 ± 0.083 | >1 | 0.623 ± 0.087 | 0.062 ± 0.009 | N/A | −1.3 ± 0.1 |
|   | HCC1954 | $PIK3CA^{H1047R}$ | 2.405 ± 1.567 | >1 | 0.461 ± 0.249 | 0.046 ± 0.025 | N/A | 22 ± 4.6 |
|   | MDA-MB-453 | $PIK3CA^{H1047R}$ | 4.476 ± 1.467 | >1 | 2.437 ± 0.078 | 0.244 ± 0.008 | N/A | 10 ± 5.2 |
|   | BT474-J4 | $PIK3CA^{K111N}$ | >10 | >1 | 3.090 ± 2.370 | 0.309 ± 0.237 | N/A | 18 ± 0.2 |
|   | JimT-1 | $PIK3CA^{C420R}$ | >10 | >1 | >10 | >1 | N/A | N/A |
| II | MDAMB175VII | WT | 0.146 ± 0.035 | 0.133 ± 0.097 | 0.059 ± 0.006 | 0.006 ± 0.001 | 0.51 ± 0.08 | 17 ± 3.2 |
|   | SUM149 | WT | 4.730 ± 1.372 | 0.067 ± 0.048 | 0.157 ± 0.027 | 0.016 ± 0.003 | 0.38 ± 0.31 | 13 ± 0.5 |
|   | COLO824 | WT | >10± | 0.009 ± 0.006 | 0.091 ± 0.038 | 0.009 ± 0.004 | N/A | −1 ± 2.7 |
| III | NCI-H508 | $BRAF^{G596R}$/ $PIK3CA^{E545K}$ | 0.149 ± 0.205 | 0.019 ± 0.005 | 0.019 ± 0.032 | 0.003 ± 0.003 | 0.70 ± 0.13 | 5 ± 7.1 |
|   | NCI-H747 | $KRAS\_^{G13D}$ | 2.640 ± 1.754 | 0.003 ± 0.002 | 0.012 ± 0.007 | 0.001 ± 0.001 | 0.56 ± 0.25 | 8 ± 3.9 |
|   | T84 | $KRAS^{G13D}$/ $PIK3CA^{E542K}$ | 4.277 ± 1.348 | 0.075 ± 0.039 | 0.178 ± 0.142 | 0.018 ± 0.014 | 0.26 ± 0.10 | 24 ± 1.2 |
|   | SW403 | $KRAS^{G12V}$ | 5.362 ± 1.548 | 0.005 ± 0.004 | 0.022 ± 0.026 | 0.002 ± 0.003 | 0.34 ± 0.24 | 16 ± 8.8 |
|   | LS174T | $KRAS^{G12D}$/ $PIK3CA^{H1047R}$ | 7.180 ± 3.926 | 0.099 ± 0.053 | 0.219 ± 0.142 | 0.022 ± 0.014 | 0.25 ± 0.03 | 31 ± 1.4 |
| IV | CHL1 | WT | 0.138 ± 0.004 | 0.461 ± 0.382 | 0.084 ± 0.007 | 0.008 ± 0.001 | 0.65 ± 0.07 | 11 ± 0.5 |
|   | SKMEL5 | $BRAF^{V600E}$ | 4.744 ± 1.083 | 0.003 ± 0.000 | 0.021 ± 4.6E−06 | 0.002 ± 5E−07 | 0.80 ± 0.10 | 2 ± 1.3 |
|   | A375 S2 | $BRAF^{V600E}$ | >10 | 0.001 ± 0.000 | 8E−05 ± 4.6E−05 | 8E−06 ± 5.E−06 | N/A | 49 ± 0.9 |
| V | HPAF-11 | $KRAS^{G12D}$ | 10.52 ± 2.770 | 0.059 ± 0.030 | 0.281 ± 0.144 | 0.028 ± 0.014 | 0.52 ± 0.04 | 16 ± 5.7 |
|   | Capan-1 | $KRAS^{G12V}$ | >10 | 0.086 ± 0.007 | 0.216 ± 0.049 | 0.022 ± 0.005 | N/A | 10 ± 2.8 |
|   | SUIT2 | ND | >10 | 0.196 ± 0.269 | 1.029 ± 1.406 | 0.103 ± 0.141 | N/A | 8 ± 5.2 |

TABLE 1-continued

Cell growth inhibition by Compound A, Compound B and their combination in tumor cell lines.

| | Cancer Cell Lines | Gene Status RAS/RAF/ PIK3CA | Single agent IC$_{50}$ (μM), mean ± STD | | Combination IC$_{50}$ (μM), mean ± STD | | Combination Effects at IC$_{50}$ | |
|---|---|---|---|---|---|---|---|---|
| | | | Compound A | Compound B | Compound A | Compound B | CI, mean ± STD | EOHSA (ppts), mean ± STD |
| VI | BFTC-905 | NRAS$^{Q61L}$ | 4.280 ± 0.073 | 0.012 ± 0.003 | 0.035 ± 0.019 | 0.003 ± 0.002 | 0.30 ± 0.09 | 24 ± 9.7 |
| | SW780 | WT | 4.114 ± 1.389 | 0.070 ± 0.042 | 0.273 ± 0.208 | 0.060 ± 0.044 | 0.87 ± 0.19 | 2 ± 1.8 |
| | 647V | WT | >10 | >1 | 5.044 ± 1.111 | 0.504 ± 0.111 | N/A | 23 ± 0.03 |

I: Breast HER2+;
II: Breast HER2−;
III: Colorectal;
IV: Melanoma;
V: Pancreatic;
VI: Bladder.
ND: not determined;
N/A: not applicable;
CI: Combination index;
ppts: percentage of points.

Because the combinations of the present invention are active in the above assays they exhibit advantageous therapeutic utility in treating cancer.

Suitably, the present invention relates to a method for treating or lessening the severity of a cancer selected from: brain (gliomas), glioblastomas, astrocytomas, glioblastoma multiforme, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, Lymphoblastic T cell leukemia, Chronic myelogenous leukemia, Chronic lymphocytic leukemia, Hairy-cell leukemia, acute lymphoblastic leukemia, acute myelogenous leukemia, Chronic neutrophilic leukemia, Acute lymphoblastic T cell leukemia, Plasmacytoma, Immunoblastic large cell leukemia, Mantle cell leukemia, multiple myeloma Megakaryoblastic leukemia, multiple myeloma, acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

Suitably, the present invention relates to a method for treating or lessening the severity of a cancer selected from: brain (gliomas), glioblastomas, astrocytomas, glioblastoma multiforme, Bannayan-Zonana syndrome, Cowden disease, Lhermitte-Duclos disease, breast, colon, head and neck, kidney, lung, liver, melanoma, ovarian, pancreatic, prostate, sarcoma and thyroid.

Suitably, the present invention relates to a method for treating or lessening the severity of a cancer selected from ovarian, breast, pancreatic and prostate.

Suitably, the present invention relates to a method of treating or lessening the severity of a cancer that is either wild type or mutant for Ras/Raf and either wild type or mutant for PIK3CA/PTEN. This includes patients who are wild type for both Ras/Raf and PIK3CA/PTEN, mutant for both Ras/Raf and PIK3CA/PTEN, mutant for Ras/Raf and wild type for PIK3CA/PTEN and wild type for Ras/Raf and mutant for PIK3CA/PTEN. The present invention also relates to a method of treating or lessening the severity of a cancer that has an activated ERK pathway, e.g., by upregulation of a Receptor Tyrosine Kinase. The present invention also relates to a method of treating or lessening the severity of a cancer that has activated AKT, e.g., by upregulation of a Receptor Tyrosine Kinase, by mutation or amplification of AKT1, AKT2 or AKT3 genes. The present invention also relates to a method of treating or lessening the severity of a cancer that has activated EGFR or ErbB-2, e.g., by mutation, amplification of the gene or over expression of the protein.

The term "wild type" as is understood in the art refers to a polypeptide or polynucleotide sequence that occurs in a native population without genetic modification. As is also understood in the art, a "mutant" includes a polypeptide or polynucleotide sequence having at least one modification to an amino acid or nucleic acid compared to the corresponding amino acid or nucleic acid found in a wild type polypeptide or polynucleotide, respectively. Included in the term mutant is Single Nucleotide Polymorphism (SNP) where a single base pair distinction exists in the sequence of a nucleic acid strand compared to the most prevalently found (wild type) nucleic acid strand.

Cancers that are either wild type or mutant for Ras/Raf, PIK3CA/PTEN, AKT, EGFR or ErbB-2 or have amplification of PIK3CA, AKT, EGFR or ErbB-2 genes or have over expression of EGFR, ErbB2 or another Receptor Tyrosine Kinase protein are identified by known methods.

For example, wild type or mutant Ras/Raf, PIK3CA/PTEN, AKT EGFR or ErbB-2 tumor cells can be identified by DNA amplification and sequencing techniques, DNA and RNA detection techniques, including, but not limited to Northern and Southern blot, respectively, and/or various biochip and array technologies or in-situ hybridization. Wild type and mutant polypeptides can be detected by a variety of techniques including, but not limited to immunodiagnostic techniques such as ELISA, Western blot or immunocytochemistry.

This invention provides a combination comprising N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate and/or salt thereof, suitably the ditosylate monohydrate salt thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, suitably the dimethyl sulfoxide solvate thereof.

This invention also provides for a combination comprising N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate and/or salt thereof, suitably the ditosylate monohydrate salt, thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, suitably the dimethyl sulfoxide solvate thereof, for use in therapy.

This invention also provides for a combination comprising N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate and/or salt thereof, suitably the ditosylate monohydrate salt, thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, suitably the dimethyl sulfoxide solvate thereof, for use in treating cancer.

This invention also provides a pharmaceutical composition comprising a combination of N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate and/or salt thereof, suitably the ditosylate monohydrate salt, thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, suitably the dimethyl sulfoxide solvate thereof.

This invention also provides a combination kit comprising N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate and/or salt thereof, suitably the ditosylate monohydrate salt, thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, suitably the dimethyl sulfoxide solvate thereof.

This invention also provides for the use of a combination comprising N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate and/or salt thereof, suitably the ditosylate monohydrate salt, thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, suitably the dimethyl sulfoxide solvate thereof, in the manufacture of a medicament.

This invention also provides for the use of a combination comprising N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate and/or salt thereof, suitably the ditosylate monohydrate salt, thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, suitably the dimethyl sulfoxide solvate thereof, in the manufacture of a medicament to treat cancer.

This invention also provides a method of treating cancer which comprises administering a combination of N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate and/or salt thereof, suitably the ditosylate monohydrate salt, thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, suitably the dimethyl sulfoxide solvate thereof, to a subject in need thereof.

The following examples are intended for illustration only and are not intended to limit the scope of the invention in any way.

EXPERIMENTAL DETAILS

Example 1

Capsule Composition

An oral dosage form for administering a combination of the present invention is produced by filing a standard two piece hard gelatin capsule with the ingredients in the proportions shown in Table I, below.

TABLE I

| INGREDIENTS | AMOUNTS |
| --- | --- |
| N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate (the ditosylate monohydrate salt of Compound A) | 250 mg |
| N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide dimethyl sulfoxide (the dimethyl sulfoxide solvate of Compound B) | 5 mg |
| Mannitol | 250 mg |
| Talc | 125 mg |
| Magnesium Stearate | 8 mg |

Example 2

Capsule Composition

An oral dosage form for administering one of the compounds of the present invention is produced by filing a standard two piece hard gelatin capsule with the ingredients in the proportions shown in Table II, below.

TABLE II

| INGREDIENTS | AMOUNTS |
| --- | --- |
| N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate (the ditosylate monohydrate salt of Compound A) | 250 mg |
| Mannitol | 55 mg |
| Talc | 16 mg |
| Magnesium Stearate | 4 mg |

Example 3

Capsule Composition

An oral dosage form for administering one of the compounds of the present invention is produced by filing a standard two piece hard gelatin capsule with the ingredients in the proportions shown in Table III, below.

TABLE III

| INGREDIENTS | AMOUNTS |
| --- | --- |
| N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide dimethyl sulfoxide (the dimethyl sulfoxide solvate of Compound B) | 5 mg |
| Mannitol | 250 mg |
| Talc | 125 mg |
| Magnesium Stearate | 8 mg |

Example 4

Tablet Composition

The sucrose, microcrystalline cellulose and the compounds of the invented combination, as shown in Table IV below, are mixed and granulated in the proportions shown with a 10% gelatin solution. The wet granules are screened, dried, mixed with the starch, talc and stearic acid, then screened and compressed into a tablet.

TABLE IV

| INGREDIENTS | AMOUNTS |
| --- | --- |
| N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate (the ditosylate monohydrate salt of Compound A) | 250 mg |
| N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide dimethyl sulfoxide (the dimethyl sulfoxide solvate of Compound B) | 5 mg |
| Microcrystalline cellulose | 300 mg |
| sucrose | 10 mg |
| starch | 40 mg |
| talc | 20 mg |
| stearic acid | 5 mg |

Example 5

Tablet Composition

The sucrose, microcrystalline cellulose and one of the compounds of the invented combination, as shown in Table V below, are mixed and granulated in the proportions shown with a 10% gelatin solution. The wet granules are screened, dried, mixed with the starch, talc and stearic acid, then screened and compressed into a tablet.

TABLE V

| INGREDIENTS | AMOUNTS |
| --- | --- |
| N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate (the ditosylate monohydrate salt of Compound A) | 250 mg |
| Microcrystalline cellulose | 30 mg |
| sucrose | 4 mg |
| starch | 2 mg |
| talc | 1 mg |
| stearic acid | 0.5 mg |

Example 6

Tablet Composition

The sucrose, microcrystalline cellulose and one of the compounds of the invented combination, as shown in Table VI below, are mixed and granulated in the proportions shown with a 10% gelatin solution. The wet granules are screened, dried, mixed with the starch, talc and stearic acid, then screened and compressed into a tablet.

TABLE VI

| INGREDIENTS | AMOUNTS |
| --- | --- |
| N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide dimethyl sulfoxide (the dimethyl sulfoxide solvate of Compound B) | 5 mg |
| Microcrystalline cellulose | 300 mg |
| sucrose | 40 mg |
| starch | 20 mg |
| talc | 10 mg |
| stearic acid | 5 mg |

While the preferred embodiments of the invention are illustrated by the above, it is to be understood that the invention is not limited to the precise instructions herein disclosed and that the right to all modifications coming within the scope of the following claims is reserved.

We claim:

1. A combination comprising:
    (i) a compound of Structure (I):

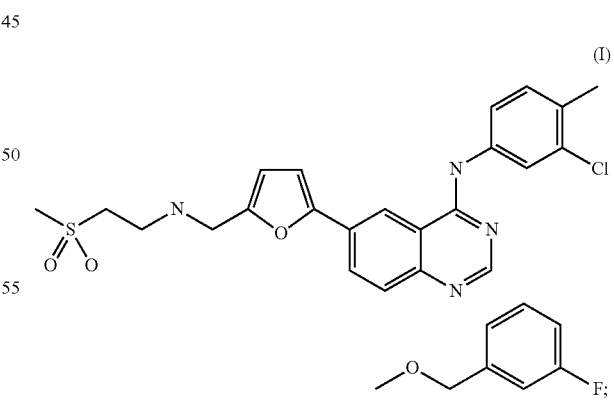

or a pharmaceutically acceptable hydrate or salt thereof; and (ii) a compound N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide

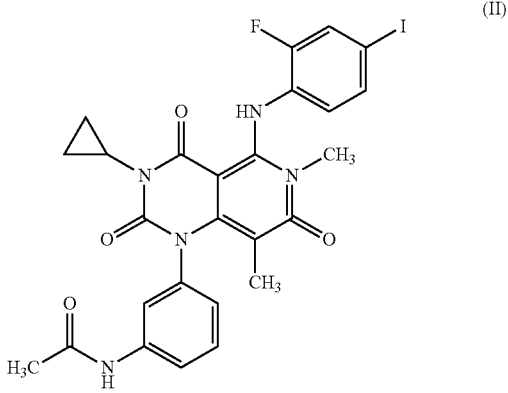

(II)

or a pharmaceutically acceptable salt or solvate thereof.

2. A combination according to claim 1 where the compound of Structure (I) is in the form of a ditosylate monohydrate salt and the compound N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide is in the form of a dimethyl sulfoxide solvate.

3. A combination kit comprising a combination according to claim 1 together with a pharmaceutically acceptable carrier or carriers.

4. A combination according to claim 1 where the amount of the compound of Structure (I) is an amount selected from 750 mg to 1,250 mg, and that amount is administered once per day in one or more tablets, and the amount of the compound N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide is an amount selected from 0.125 mg to 10 mg, and that amount is administered once per day.

5. A method of treating cancer in a human in need thereof which comprises the in vivo administration of a therapeutically effective amount of a combination of N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate or salt thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, to such human,
wherein the combination is administered within a specified period, and
wherein the combination is administered for a duration of time.

6. A method according to claim 5 wherein the amount of N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate or salt thereof, is selected from about 750 mg to about 1,250 mg, and that amount is administered once per day in one or more tablets, and the amount of N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt of solvate thereof, is selected from about 0.125 mg to about 10 mg, and that amount is administered once per day.

7. A method according to claim 6 wherein the amount of N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate or salt thereof, is selected from about 750 mg to about 1,250 mg, and that amount is administered once per day in one or more tablets, and the amount of N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide dimethyl sulfoxide is selected from about 1 mg to about 9 mg, and that amount is administered once per day.

8. A method according to claim 7 wherein the compound N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate or salt thereof is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate and the N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt of solvate thereof is N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide dimethyl sulfoxide, and wherein N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide dimethyl sulfoxide, are administered within 12 hours of each other for from 1 to 3 consecutive days followed by administration of N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate for from 3 to 7 consecutive days, optionally followed by one or more cycles of repeat dosing.

9. A method according to claim 5 wherein the cancer is selected from: brain, glioblastomas, astrocytomas, glioblastoma multiforme, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid,
Lymphoblastic T cell leukemia, Chronic myelogenous leukemia, Chronic lymphocytic leukemia, Hairy-cell leukemia, acute lymphoblastic leukemia, acute myelogenous leukemia, Chronic neutrophilic leukemia, Acute lymphoblastic T cell leukemia, Plasmacytoma, Immunoblastic large cell leukemia, Mantle cell leukemia, Multiple myeloma Megakaryoblastic leukemia, multiple myeloma, acute megakaryocytic leukemia, promyelocytic leukemia, Erythroleukemia,
malignant lymphoma, hodgkins lymphoma, non-hodgkins lymphoma, lymphoblastic T cell lymphoma, Burkitt's lymphoma, follicular lymphoma,
neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

10. A method according to claim 9 wherein the amount of N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate or salt thereof, is selected from about 750 mg to about 1,250 mg, and that amount is administered once per day in one or more tablets, and the amount of N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, is selected from about 0.125 mg to about 10 mg, and that amount is administered once per day.

11. A method according to claim 10 wherein the amount of N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate or salt thereof, is selected from about 750 mg to about 1,250 mg, and that amount is administered once per day in one or more tablets, and the amount of N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, is selected from about 0.5 mg to about 9 mg, and that amount is administered once per day.

12. A method according to claim 11 wherein the N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate or salt thereof is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate and the N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt of solvate thereof is N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide dimethyl sulfoxide, and wherein N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide dimethyl sulfoxide are administered within 12 hours of each other for at least 14 days.

13. A method according to claim 9 wherein the cancer selected from ovarian, breast, pancreatic and prostate.

14. A method according to claim 10 wherein the cancer selected from ovarian, breast, pancreatic and prostate.

15. A method according to claim 12 wherein the cancer selected from ovarian, breast, pancreatic and prostate.

16. A method treating a cancer selected from: brain, glioblastomas, astrocytomas, glioblastoma multiforme, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, Lymphoblastic T cell leukemia, Chronic myelogenous leukemia, Chronic lymphocytic leukemia, Hairy-cell leukemia, acute lymphoblastic leukemia, acute myelogenous leukemia, Chronic neutrophilic leukemia, Acute lymphoblastic T cell leukemia, Plasmacytoma, Immunoblastic large cell leukemia, Mantle cell leukemia, Multiple myeloma Megakaryoblastic leukemia, multiple myeloma, acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer;

in a human in need thereof which comprises the in vivo administration of a therapeutically effective amount of a combination of N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate or salt thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, to such human, wherein the compounds of the combination are administered sequentially.

17. A method according to claim 16 wherein the amount of N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate or salt thereof, is selected from about 750 mg to about 1,250 mg, and that amount is administered once per day in one or more tablets, and the amount of N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, is selected from about 0.125 mg to about 10 mg, and that amount is administered once per day.

18. A method according to claim 17 wherein the amount of N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate or salt thereof, is selected from about 750 mg to about 1,250 mg, and that amount is administered once per day in one or more tablets, and the amount of N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, is selected from about 0.5 mg to about 9 mg, and that amount is administered once per day.

19. A method according to claim 18 wherein the N-{3-Chloro-4-[(3-fluorobenzyl)oxy]phenyl}-6-[5-({[2-(methanesulphonyl)ethyl]amino}methyl)-2-furyl]-4-quinazolinamine, or a pharmaceutically acceptable hydrate or salt thereof is N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate and the N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt of solvate thereof is N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide dimethyl sulfoxide, and wherein N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate is administered for from 1 to 30 consecutive days, followed by an optional drug holiday of from 1 to 14 days, followed by administration of N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide dimethyl sulfoxide for from 1 to 30 days, optionally followed by one or more cycles of repeat dosing.

20. A method according to claim 16 wherein the cancer selected from ovarian, breast, pancreatic and prostate.

* * * * *